United States Patent
Green et al.

(10) Patent No.: US 6,956,139 B2
(45) Date of Patent: Oct. 18, 2005

(54) (1R, 2S, 5R)-3-1-MENTHOXYALKAN-1-OL COOLING SENSATE

(75) Inventors: Carter B. Green, Stony Point, NY (US); Tetsuo Nakatsu, Chappaqua, NY (US); Takero Ishizaki, Shizuoka (JP); Andrew T. Lupo, Jr., Emerson, NJ (US)

(73) Assignees: Takasago International Corporation, Tokyo (JP); Takasago International Corporation (U.S.A.), Rockleigh, NJ (US)

( * ) Notice: Subject to any disclaimer, the term of this patent is extended or adjusted under 35 U.S.C. 154(b) by 0 days.

(21) Appl. No.: 10/170,123

(22) Filed: Jun. 10, 2002

(65) Prior Publication Data

US 2002/0198412 A1 Dec. 26, 2002

Related U.S. Application Data

(63) Continuation of application No. 09/514,554, filed on Feb. 28, 2000, now abandoned.

(51) Int. Cl.$^7$ .......................... C07C 41/00; C07C 35/12; A23L 1/22; A61K 7/16
(52) U.S. Cl. ...................... 568/666; 568/670; 568/829; 426/534; 424/49
(58) Field of Search ................. 568/666, 670, 568/829; 426/534; 424/49

(56) References Cited

U.S. PATENT DOCUMENTS 4,029,759 A   6/1977   Humbert et al. .............. 424/49
4,459,425 A   7/1984   Amano et al. .............. 568/666
4,749,811 A * 6/1988   Cesa et al. .................. 562/589

FOREIGN PATENT DOCUMENTS

GB        1 315 626        2/1971     ............ A61K/7/16

OTHER PUBLICATIONS van der Zeijden et al. Synthesis of Chrial O–Functionalized Isobornyloxy, Menthyloxy and Fenchyloxy Cyclopentadienyl Ligands. Synthesis, 1996, vol. 7, p 847–850.*

Kyoji Turata et al., "A Direct Synthesis fo Cyclic Acetals from β– or γ–Hydroxy Ethers by Means of C–H Activation," *Tetrahedron Letters*, vol. 29, No. 18: 2215–2218 (1998).

* cited by examiner

Primary Examiner—Johann Richter
Assistant Examiner—Sikarl A. Witherspoon
(74) Attorney, Agent, or Firm—Darby & Darby

(57) ABSTRACT

A cooling sensate compound having the general formula (I):

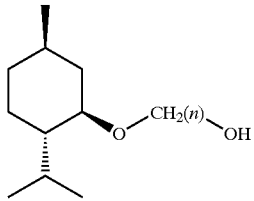

(I)

where n is an integer from 2 to 6. The compound is effective in imparting a refreshing and cooling sensation of long duration. A cooling sensate composition having the general formula (I) is used in a variety of formulations to impart the refreshing and cooling sensation. These cooling sensates are useful in a variety of consumer products including mouth formulations, food products and toiletries.

13 Claims, No Drawings

(1R, 2S, 5R)-3-1-MENTHOXYALKAN-1-OL COOLING SENSATE

RELATED APPLICATIONS

This application is a continuation of U.S. patent application Ser. No. 09/514,554 filed Feb. 28, 2000, now abandoned.

BACKGROUND OF THE INVENTION

The present invention relates to enantiomeric menthoxyalkan-1-ol compounds which function as cooling sensates. These compounds are useful as fragrance and flavor compounds in products such as toothpastes, skin lotions and hard candies and other confections.

Substances giving a physiologically cooling and/or refreshing feeling to the human skin or membranes, in particular to the membranes in the mouth, nose, throat, are well known. A representative example is 1-menthol. L-menthol is widely used as a flavor substance which imparts a desirable cooling and/or refreshing feeling. L-menthol is widely used in oral formulations, such as toothpaste and chewing gums; in food and beverage products, such as sherbet and hard candy; and in toiletry products, such as cosmetics and eye pack materials. However, 1-menthol has a strong minty smell and is also volatile. Although 1-menthol has a strong cooling and/or refreshing effect, the effect is not long-lasting.

Other compounds having an effect similar to that of 1-menthol are known. For example, 3-substituted-p-menthane compounds (Japanese Laid Open Patent Number 47-16,647, Japanese Laid Open Patent Number 47-16,649, British Patent Number 1,315,626), N-substituted-p-menthane-3-carboxamide compounds (Japanese Laid Open Patent Number 47-16,648), paramenthanediol compounds (Japanese Laid Open Patent Number 47-16,650), and 3-1-menthoxypropane-1, 2-diol (Japanese Examined Patent Number 61-48,813, U.S. Pat. No. 4,459,425) are disclosed which have an effect similar to that of 1-menthol. Furthermore Japanese Laid Open Patent Number 7-82,200 discloses (2R)-3-{(1R,2S,5R)-[5-methyl-2-(1-methyethyl) cyclohexyl]oxy}-1,2-propanediol.

Among these compounds, the 3-1-menthoxypropan-1,2-diol compound has a low volatility, is almost odorless, and has an excellent cooling effect. Because 3-1-menthoxypropane-1,2-diol does not have an effect on the aroma or flavor of the product, it is widely used in food and beverage products and in cosmetics.

British Patent Number 1,315,626 discloses that compounds having a p-menthane framework exist in cis form or trans forms. The compounds having an equatorial orientation have a stronger cooling and/or refreshing effect compared to the same compounds having an axial orientation, and thus are preferred. For example, 3-(2-hydroxyethoxy)-p-menthane and 3-(2-hydroxy-n-propyloxy)-p-menthane have been disclosed. However, there is no disclosure regarding the relation between the absolute stereochemistry of these compounds and the cool/refreshing feeling effect. While the British Patent does disclose that the d-form has, in most cases, a greater physiological cooling effect, there is no discussion of any preferred absolute configuration. The reference only notes that four geometric isomers arise from substitution at the 3-position of the basic p-menthane structure, and that for each of these geometric isomers, there are a number of optical isomers.

In recent years, consumer preferences for food and beverage products in as well as cosmetic products have become more varied. There is an increasing desire for development of food and/or beverage products as well as cosmetic products that provide cooling and/or refreshing effects, or similar unique type flavor impressions.

OBJECTS AND SUMMARY OF THE INVENTION

In light of the above, it is an object of the present invention to overcome the limitations of the prior art.

The present inventors have discovered through intensive study, that enantiomeric compounds having a 1-menthane framework possess unexpectedly superior and longer lasting cooling sensate effects. The present invention was based on this finding.

It is an object of the present invention to provide cooling sensate compounds that provide long lasting cooling and refreshing effects.

It is another object of the present invention to provide cooling sensate compositions that are long lasting in effect.

It is another object of the present invention to provide a tooth paste containing a cooling sensate that is refreshing, cool and long lasting.

It is another object of the present invention to provide mouth formulation products using at least one compound of the present invention as a cooling sensate including mouth washes, cough drops, nebulizers, inhalants and other related products.

It is another object of the present invention to provide food products using at least one compound of the present invention as a cooling sensate including fruit juices, fruit wines, dairy drinks, carbonated drinks, ice cream, sherbet, ice candy, jelly, hard candy and related products.

It is another object of the present invention to provide a cooling sensate composition including an enantiomeric compound having a 1-menthane framework along with at least one additional sensate compound to give rise to additional novel sensate effects.

It is another object of the present invention to provide toiletry products using at least one compound of the present invention as a cooling sensate including eau de toilette, lotion, milky lotion, facial packs, hair care products, soap, anti-perpirants, deodorizers, after shave lotions, and other related products.

Briefly stated the present invention relates to a (1R,2S, 5R)-3-1-menthoxyalkan-1-ol represented by the following formula (I).

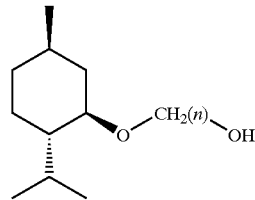

(I)

wherein n is an integer from 2 to 6.

The present invention has a cooling and refreshing effect when in contact with human skin or membranes, and is useful as a flavor compound. The present invention further relates to oral formulations, food or beverage products, or toiletry products which contain a (1R,2S,5R)-3-1-menthoxyalkan-1-ol represented by the above formula (I).

According to an embodiment of the present invention, a cooling sensate comprises the enantiomer (1R,2S,5R)-3-(1-menthoxy)propan-1-ol.

According to another embodiment of the present invention, a cooling sensate comprises the enantiomer (1R, 2S,5R)-2-(5-methyl-2-(methyethyl)-cyclohexyloxy)-ethan-1-ol.

According to another embodiment of the present invention, a cooling sensate comprises the enantiomer (1R, 2S,5R)-3-(5-methyl-2-(methylethyl)-cyclohexyloxy)-butan-1-ol.

According to another embodiment of the present invention, a mouth formulation comprises at least one of the enantiomers of the present invention in addition to relevant additives and other ingredients.

According to another embodiment of the present invention, a flavor formulation comprises at least one of the enantiomers of the present invention in addition to relevant additives and other ingredients.

According to another embodiment of the present invention, a food or beverage formulation comprises at least one of the enantiomers of the present invention in addition to relevant additives and other ingredients.

The above, and other objects, features and advantages of the present invention will become apparent from the following description of preferred embodiments and comparative examples.

DETAILED DESCRIPTION OF THE PREFERRED EMBODIMENT

The present inventors have discerned that among the known compounds which have a cooling and/or refreshing effect, such as menthoxypropan-1,2-diol, there is a common characteristic of having a p-menthane framework. However, these compounds are known to be racemic mixtures. The cooling sensates of the present invention also contain the p-menthane framework. However, unlike the known cooling sensates, the present inventions are enantiomers. Compounds were discovered that have excellent cool/refreshing properties and are long lasting, compared with the well-known compounds 1-menthol and menthoxypropane-1,2-diol.

Example 1 describes the preparation of (1R,2S, 5R)-2-(5-methyl-2-(methylethyl)-cyclohexyloxy)-ethan-1-ol, a compound of the present invention where n=2.

Example 2 describes the preparation of (1R,2S, 5R)-3-(5-methyl-2-(methylethyl)-cyclohexyloxy)-ethan-1-ol, a compound of the present invention where n=3.

Example 3 describes the preparation of (1R,2S, 5R)-4-(5-methyl-2-(methylethyl)-cyclohexyloxy)-ethan-1-ol, a compound of the present invention where n=4.

As described above, the compounds of the present invention, as exemplified by synthesis of (1R,2S,5R)-3-1-menthoxypropan-1-ol, can be obtained through easily obtained raw materials, through short processes, and without complicated operations.

The compounds of the present invention have low volatility and are very nearly odorless liquids. They have an unexpectedly superior cooling and/or refreshing effect of long-lasting duration. The compounds of the present invention can be added to and used in a variety of flavor formulations, in formulations for the mouth, in food and beverage products, and in toiletry products.

Although it depends on the objective and the type of flavor formulation, when using the compound of the present invention in various flavor formulations, it is normally mixed in from about 1 to about 95% by weight of the overall flavor formulation. The preferred range is from about 1 to about 30% by weight of the overall flavor formulation. For use in mouth formulations, such as, but not limited to, paste toothpaste, powder toothpaste, gel toothpaste and chewing gum, the present invention is combined from about 1 to about 25% by weight of the overall flavor formulation. The preferred range is from about 1 to about 15% by weight of the flavor formulation.

For use in food and beverage products, such as, but not limited to, fruit juices, fruit wines, dairy drinks, carbonated drinks, ice cream, sherbet, ice candy, jelly and hard candy the present invention is combined from about 1 to about 25% by weight of the flavor formulation of the food and beverage product. The preferred range is from about 1 to about 15% by weight of the flavor formulation.

For use in toiletries, such as, but not limited to, eau de toilette, lotion, milky lotion, facial creams, facial packs, hair toiletries, shampoos, face cleansers, anti-perspirants, and deodorants, the present invention is combined from about 1 to about 20% by weight of the fragrance formulation of the toiletry product. The preferred range is from about 1 to about 10% by weight of the fragrance formulation.

In these flavor formulations, mouth formulations, food and beverage products, and toiletries, appropriate components other than the compound of the present invention can be freely chosen. The selection of these additional components will be apparent to one of ordinary skill in the art.

For example, for a facial cream, additional ingredients such as an emulsifier, fragrance, antiseptic agents, pigments, nutritive agents, moisturizers and ultraviolet protection can be selected and blended using standard methods. Similarly, eau de toilette, lotion, milky lotion, facial packs, hair care products, soap, anti-perspirants, deodorizers can also have varying components selected and as required depending on the type of product.

Analysis of the examples was conducted by using the following analytical equipment. Column chromatogram: 5890-A (Hewlett-Packard Company) Column: Chemical Bounded Column OV-1 25 mm×0.25 mm ID 0.15 Mm (GL Science Company) Temperature: 70–220 degrees C. (heated at 4° C./minute) Degree of optical rotation: DIP-370 model (Japan Spectral Industry Company).

COMPARATIVE EXAMPLE 1

Preparation of (d,l)-2-(5'-methyl-2'-(methylethyl) cyclohexyloxy)ethan-1-ol

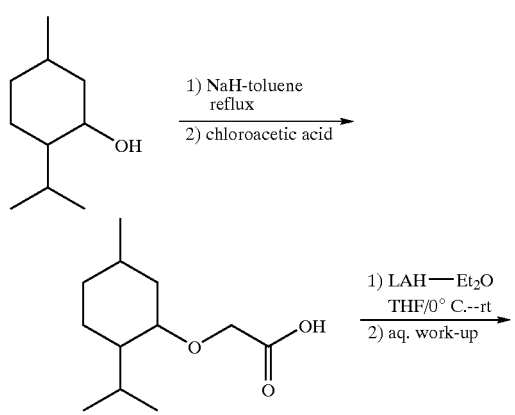

-continued

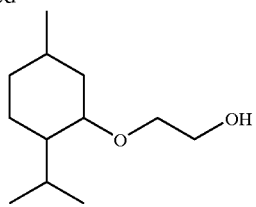

Preparation of (d,l)-2-(5'-methyl-2'-(methylethyl) cyclohexyloxy)acetic Acid (d,l)-2-(5'-Methyl-2'-(methylethyl)cyclohexyloxy)acetic acid was prepared from (d,l)-menthol as described in the literature (Org. Syn. Coll. Vol. III, p. 544), with sodium hydride being used in place of sodium metal. From (d,l)-menthol (20.0 g, 0.128 moles) was obtained (d,l)-2-(5'-methyl-2'-(methylethyl)cyclohexyloxy)acetic acid (20.05 g, 73.2% yield).

The CAS registry number is 71420-37-6. The molecular formula is $C_{12}H_{22}O_3$ and the molecular weight is 214.30. The boiling point is 109° C. at 0.38 mm Hg.

500 MHz $^1$H-NMR analysis in $CDCl_3$ provided the following data: δ 0.76 (d, 3H), 0.79–1.0 (m, 3H), 0.88 (d, 3H), 0.90 (d, 3H), 1.26–1.38 (m, 2H), 1.59–1.67 (m, 2H), 2.01–2.06 (m, 1H), 2.16–2.20 (m, 1H), 3.18 (dt, 1H), 4.07 (d, 1H), 4.18 (d, 1H), 9.70 (bs, 1H).

125 MHz $^{13}$C-NMR analysis in $CDCl_3$ provided the following data: δ 16.14, 20.88, 22.16, 23.19, 25.63, 31.45, 34.27, 39.87, 47.92, 65.42, 80.63, 174.59.

IR analysis provided the following data ($v_{max}(cm^{-1})$): 3060 (m), 2950 (s), 1760 (s), 1460 (m), 1240 (w), 1120 (s).

MS analysis provided the following data (m/z): 155 $(M-59)^+$, 143, 138, 129, 123, 115, 109, 95, 81, 71, 55, 41.

Preparation of (d,l)-2-(5'-methyl-2'-(methylethyl) cyclohexyloxy)ethan-1-ol

A 1.0 M solution of LAH-$Et_2O$ (32.7 mL) was added drop-wise to an ice cold stirred solution of (d,l)-2-(5'-methyl-2'-(methylethyl)cyclohexyloxy)acetic acid (8.0 g, 0.037 moles) in 200 mL of anhydrous THF. After addition the mixture was allowed to warm to room temperature with continued stirring for 6 h. Water (1 mL) is cautiously added drop-wise, followed by the drop-wise addition of 3.0 M NaOH (1 mL) and water (3.0 mL). This mixture was stirred at room temperature for 1 hr, followed by transfer to a separatory funnel. The organic layer was separated and washed successively with 10% HCl, sat. $NaHCO_3$, and brine, followed by drying over $MgSO_4$. After solvent removal under reduced pressure, the pale yellow oil was distilled under vacuum to give (d,l)-2-(5'-methyl-2'-(methylethyl)cyclohexyloxy)ethan-1-ol (5.5 g, 73.3% yield).

The CAS registry number is 38618-23-4. The molecular formula is $C_{12}H_{24}O_2$ and the molecular weight is 200.32. The boiling point is 70° C. at 0.5 mm Hg.

500 MHz $^1$H-NMR analysis in $CDCl_3$ provided the following data: δ 0.76 (d, 3H), 0.79–0.86 (m, 2H), 0.88 (d, 3H), 0.90 (d, 3H), 0.92–1.00 (m, 2H), 1.20–1.24 (m, 1H), 1.29–1.38 (m, 1H), 1.58–1.66 (m, 2H), 2.05–2.10 (m, 1H), 2.12–2.20 (m, 2H), 3.06 (dt, 1H), 3.37–3.42 (m, 1H), 3.65–3.72 (m, 3H).

125 MHz $^{13}$C-NMR analysis in $CDCl_3$ provided the following data: δ 16.21, 20.92, 22.28, 23.35, 25.76, 31.51, 34.52, 40.45, 48.26, 62.27, 69.39, 79.54.

IR analysis provided the following data ($v_{max}(cm^{-1})$): 3425 (m), 2950 (s), 1460 (m), 1340 (w), 1110 (s), 1050 (s).

MS analysis provided the following data (m/z): 200 $(M^+)$, 185, 169, 157, 138, 123, 115, 95, 81, 71, 55, 41.

Example 1

Preparation of [1'R,2'S,5'R]-2-(5'-methyl-2'-(methylethyl)cyclohexyloxy)ethan-1-ol

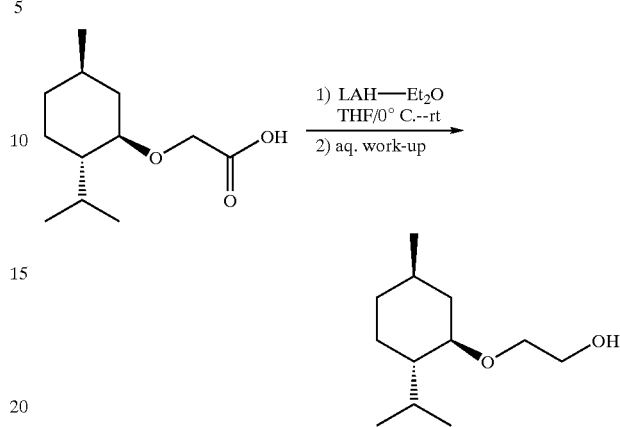

Preparation of [1'R,2'S,5'R]-2-(5'-methyl-2'-(methylethyl) cyclohexyloxy)acetic Acid

[1'R,2'S,5'R]-2-(5'-methyl-2'-(methylethyl) cyclohexyloxy)acetic acid was purchased from Aldrich Chemical Co. and was used without further purification. [Alternatively, [1'R,2'S,5'R]-2-(5'-methyl-2'-(methylethyl)cyclohexyloxy) acetic acid can be prepared as described in the literature from (1)-menthol (Org. Syn. Coll. Vol. III, p. 544) or as described above for the preparation of (d,l)-2-(5'-methyl-2'-(methylethyl)cyclohexyloxy)acetic acid.]

Preparation of [1'R,2'S,5'R]-2-(5'-methyl-2'-(methylethyl) cyclohexyloxy)ethan-1-ol A 1.0 M solution of LAH-$Et_2O$ (37 mL) was added drop-wise to an ice cold stirred solution of [1'R,2'S,5'R]-2-(5'-methyl-2'-(methylethyl)cyclohexyloxy)acetic acid (8.0 g, 0.037 moles) in 200 mL of anhydrous THF. After addition the mixture was allowed to warm to room temperature with continued stirring for 6 h. Water (1 mL) is cautiously added drop-wise, followed by the drop-wise addition of 3.0 M NaOH (1 mL) and water (3.0 mL). This mixture was stirred at room temperature for 1 hr, followed by transfer to a separatory funnel. The organic layer was separated and washed successively with 10% HCl, sat. $NaHCO_3$, and brine, followed by drying over $MgSO_4$. After solvent removal under reduced pressure, the pale yellow oil was distilled under vacuum to give [1'R,2'S,5'R]-2-(5'-methyl-2'-(methylethyl)cyclohexyloxy)ethan-1-ol (6.4 g, 85.7% yield).

The CAS registry number is 75443-64-0. The molecular formula is $C_{12}H_{24}O_2$ and the molecular weight is 200.32. The boiling point is 70° C. at 0.5 mm Hg.

500 MHz $^1$H-NMR analysis in $CDCl_3$ provided the following data: δ 0.76 (d, 3H), 0.79–0.86 (m, 2H), 0.88 (d, 3H), 0.90 (d, 3H), 0.92–1.00 (m, 2H), 1.20—1.24 (m, 1H), 1.29–1.38 (m, 1H), 1.58–1.66 (m, 2H), 2.05–2.10 (m, 1H), 2.12–2.20 (m, 2H), 3.06 (dt, 1H), 3.37–3.42 (m, 1H), 3.65–3.72 (m, 3H).

125 MHz $^{13}$C-NMR analysis in $CDCl_3$ provided the following data: δ 16.29, 21.00, 22.35, 23.44, 25.84, 31.59, 34.60, 40.52, 48.34, 62.35, 69.47, 79.61.

IR analysis provided the following data ($v_{max}(cm^{-1})$): 3410 (m), 2950 (s), 1460 (m), 1340 (w), 1110 (s), 1050 (s).

MS analysis provided the following data (m/z): 200 $(M^+)$, 185, 169, 157, 138, 123, 115, 95, 81, 71, 55, 41.

EXAMPLE 2

Preparation of [1'R,2'S,5'R]-3-(5'-methyl-2'-(methylethyl)cyclohexyloxy)propan-1-ol

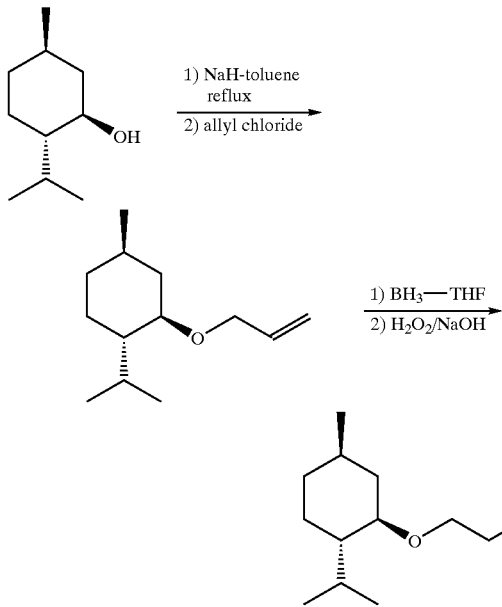

Preparation of [1'R,2'S,5'R]-1-(5-methyl-2-(methylethyl)cyclohexyloxy)prop-2-ene To a solution of (1)-menthol (30.0 g, 0.19 moles) in anhydrous toluene (300 mL) was added sodium hydride (11.5 g, 0.29 moles) in several small portions. The reaction flask was equipped with a water-cooled reflux condenser and the mixture was vigorously refluxed for 72 hours. The reaction vessel was allowed to cool to room temperature and allyl bromide (32.6 g, 0.27 moles) was added drop-wise over 1 hr. The resulting mixture was gently refluxed for 3 hr, cooled to room temperature, and the excess sodium hydride decomposed with careful drop-wise addition of water. The organic layer was separated and washed successively with 10% HCl, sat. $NaHCO_3$, and brine, followed by drying over anhydrous $MgSO_4$. After solvent removal under reduced pressure, the pale yellow oil was distilled under vacuum to give [1'R,2'S,5'R]-1-(5'-methyl-2'-(methylethyl)cyclohexyloxy)prop-2-ene (34.3 g, 92% yield).

The CAS registry number is 67528-21-6. The molecular formula is $C_{13}H_{24}O$ and the molecular weight is 196.33. The boiling point is 56° C. at 1.0 mm Hg.

500 MHz $^1$H-NMR analysis in $CDCl_3$ provided the following data: δ 0.76 (d, 3H), 0.88 (d, 3H), 0.90 (d, 3H), 0.79–1.00 (m, 3H), 1.19–1.26 (m, 1H), 1.28–1.37 (m, 1H), 1.57–1.66 (m, 2H), 2.05–2.10 (m, 1H), 2.18–2.25 (m, 1H), 3.06 (dt, 1H), 3.84–3.90 (m, 1H), 4.08–4.14 (m, 1H), 5.10–5.13 (m, 1H), 5.22–5.27 (m, 1H), 5.88–5.96 (m, 1H).

125 MHz $^{13}$C-NMR analysis in $CDCl_3$ provided the following data: δ 16.33, 21.02, 22.40, 23.49, 25.64, 31.62, 34.64, 40.59, 48.36, 69.58, 78.80, 116.31, 135.83.

IR analysis provided the following data ($v_{max}(cm^{-1})$): 3080 (w), 2960 (s), 2940 (s), 2875 (s), 1735 (w), 1650 (w), 1460 (m), 1375 (m), 1090 (m), 920 (m).

MS analysis provided the following data (m/z): 196 (M$^+$), 181, 167, 138, 123, 111, 95, 81, 69, 55, 41.

Preparation of [1'R,2'S,5'R]-3-(5'-methyl-2'-(methylethyl)cyclohexyloxy)propan-1-ol A 1M solution of $BH_3$-THF (32 mL) is added drop-wise to a stirred solution of [1'R,2'S,5'R]-1-(5-methyl-2-(methylethyl)cyclohexyloxy)prop-2-ene (11.5 g, 0.06 moles) in 100 mL of anhydrous THF at room temperature under nitrogen. After stirring at room temperature for 1 hr, water (15 mL) is added drop-wise followed by the addition of 20 mL of 3MNaOH. Hydrogen peroxide (30% aq., 20 mL) is added drop-wise such that the temperature remains between 30–50° C. When the addition is complete, stirring is continued for 1 h. Fresh diethyl ether (100 mL) is added to the reaction mixture, which is sequentially washed with ice water (2×) and brine, followed by drying over $MgSO_4$. After solvent removal under reduced pressure, the pale yellow oil was distilled under vacuum to give [1'R,2'S,5'R]-3-(5'-methyl-2'-(methylethyl)cyclohexyloxy)propan-1-ol (8.7 g, 70.2% yield).

The molecular formula is $C_{13}H_{26}O_2$ and the molecular weight is 214.34. The boiling point is 80° C. at 0.42 mm Hg.

500 MHz $^1$H-NMR analysis in $CDCl_3$ provided the following data: δ 0.76 (d, 3H), 0.82 (m, 1H), 0.87 (d, 3H), 0.91 (d, 3H), 0.94 (m, 1H), 1.18 (m, 1H), 1.32 (m, 1H), 1.60 (m, 2H), 1.80 (m, 2H), 2.11 (m, 2H), 2.24 (bs, 1H), 3.01 (m, 1H), 3.48 (m, 1H), 3.76 (t, 3H), 3.80 (m, 1H).

125 MHz $^{13}$C-NMR analysis in $CDCl_3$ provided the following data: δ 16.30, 21.01, 22.36, 23.44, 25.86, 31.62, 32.53, 34.61, 40.40, 48.34, 62.48, 67.92, 79.85.

IR analysis provided the following data ($v_{max}(cm^{-1})$): 3380 (m), 2950 (s), 1460 (w), 1110 (m), 1090 (m).

MS analysis provided the following data (m/z): 214 (M$^+$), 199, 171, 155, 138, 129, 123, 95, 81, 71, 55, 41.

EXAMPLE 3

Preparation of [1'R,2'S,5'R]-4-(5'-methyl-2'-(methylethyl)cyclohexyloxy)butan-1-ol

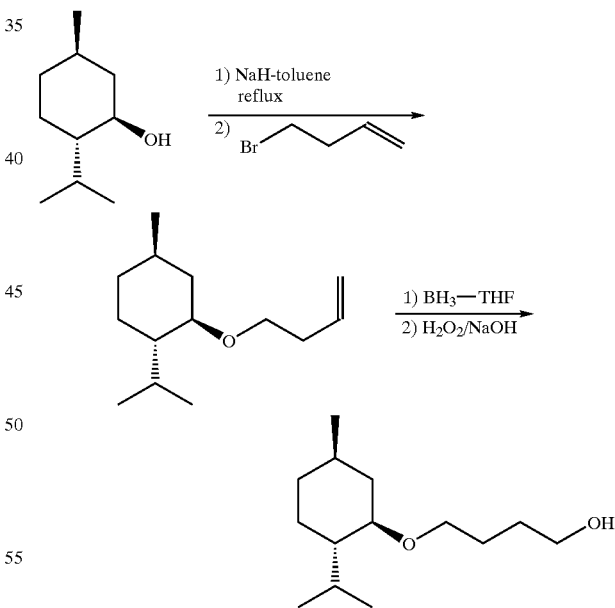

Preparation of [1'R,2'S,5'R]-1-(5-methyl-2-(methylethyl)cyclohexyloxy)but-3-ene

To a solution of (1)-menthol (23.15, 0.148 moles) in anhydrous toluene (300 mL) was added sodium hydride [60% in mineral oil dispersion] (6.2 g, 0.155 moles) in several small portions. The reaction flask was equipped with a water-cooled reflux condenser and the mixture was vigorously refluxed for 18 hours. The reaction vessel was allowed to cool to room temperature and 4-bromo-1-butene (10.0 g, 0.074 moles) was added drop-wise over 1 hr. The resulting mixture was gently refluxed for 6 hr, cooled to room temperature, and the excess sodium hydride decomposed with careful drop-wise addition of water. The organic layer was separated and washed successively with 10% HCl, sat. NaHCO$_3$, and brine, followed by drying over MgSO$_4$. After solvent removal under reduced pressure, the pale yellow was purified by flash chromatography (1:4; EtOAc:hexane) to give [1'R,2'S,5'R]-1-(5-methyl-2-(methylethyl)cyclohexyloxy)but-3-ene (1.4 g, 4.5% yield).

The molecular formula is C$_{14}$H$_{26}$O and the molecular weight is 210.36.

500 MHz $^1$H-NMR analysis in CDCl$_3$ provided the following data: δ 0.76 (d, 3H), 0.88 (d, 3H), 0.90 (d, 3H), 0.79–1.00 (m, 3H), 1.19–1.26 (m, 1H), 1.28–1.37 (m, 1H), 1.58–1.66 (m, 2H), 2.05–2.17 (m, 1H), 2.17–2.24 (m, 1H), 2.28–2.32 (m, 2H), 3.00 (dt, 1H), 3.29–3.32 (m, 1H), 3.65–3.69 (m, 1H), 5.01 (dd, 1H), 5.07 (dd, 1H), 5.78–5.88 (m, 1H).

125 MHz $^{13}$C-NMR analysis in CDCl$_3$ provided the following data: δ 16.38, 21.00, 22.41, 23.55, 25.67, 29.76, 31.65, 34.70, 40.60, 48.34, 68.04, 79.39, 116.06, 135.70.

IR analysis provided the following data ($v_{max}$(cm$^{-1}$)): 3080 (w), 2960 (s), 2925 (s), 2850 (s), 1735 (w), 1645 (w), 1460 (m), 1380 (w), 1115 (m), 1090 (w), 915 (w).

MS analysis provided the following data (m/z): 210 (M$^+$), 195, 169, 139, 125, 95, 83, 69, 55, 41.

Preparation of [1'R,2'S,5'R]-4-(5'-methyl-2'-(methylethyl)cyclohexyloxy)butan-1-ol A 1M solution of BH$_3$-THF (2.85 mL) is added drop-wise to a stirred solution of [1'R,2'S,5'R]-1-(5-methyl-2-(methylethyl)cyclohexyloxy)but-3-ene (1.2 g, 5.7 mmoles) in 10 mL of anhydrous THF at room temperature under nitrogen. After stirring at room temperature for 18 hr, water (1 mL) is added drop-wise followed by the addition of 3M NaOH (1 mL). Hydrogen peroxide (30% aq., 1.0 mL) is added drop-wise such that the temperature remains between 30–50° C. When the addition is complete, stirring is continued for 1 h. Fresh diethyl ether (20 mL) is added to the reaction mixture, which is sequentially washed with ice water (2x) and brine, followed by drying over MgSO$_4$. After solvent removal under reduced pressure, the pale yellow oil was purified by flash chromatography (1:4; EtOAc:hexane) to give [1'R,2'S,5'R]-4-(5'-methyl-2'-(methylethyl)cyclohexyloxy)butan-1-ol ((0.45 g, 35% yield).

The molecular formula is C$_{14}$H$_{28}$O$_2$ and the molecular weight is 228.37. The boiling point is 98° C. at 0.30 mm Hg.

500 MHz $^1$H-NMR analysis in CDCl$_3$ provided the following data: δ 0.76 (d, 3H), 0.78–1.00 (m, 3H), 0.88 (d, 3H), 0.90 (d, 3H), 1.18–1.24 (m, 1H), 1.28–1.40 (m, 1H), 1.52–1.74 (m, 6H), 2.06–2.12 (m, 1H), 2.14–2.20 (m, 1H), 2.53 (bs, 1H), 3.01 (dt, 1H), 3.30–3.36 (m, 1H), 3.59–3.66 (m, 3H).

125 MHz $^{13}$C-NMR analysis in CDCl$_3$ provided the following data: δ 16.38, 20.99, 22.35, 23.52, 25.79, 27.52, 30.52, 31.65, 34.61, 40.48, 48.31, 62.86, 68.47, 79.59.

IR analysis provided the following data ($v_{max}$(cm$^{-1}$)): 3360 (m), 2960 (s), 2870 (s), 1460 (m), 1370 (w), 1180 (w), 1110 (m), 1060 (m).

MS analysis provided the following data (m/z): 228 (M$^+$), 155, 138, 123, 95, 89, 81, 71, 55, 41.

Embodiment 1—Paste Toothpaste

The ingredients listed below were mixed in a suitable mixing apparatus to make paste toothpaste.

| Ingredient | Weight Percent |
| --- | --- |
| Calcium hydrogen phosphate | 51.0 |
| Glycerin | 26.0 |
| Purified water | 19.39 |
| Sodium lauryl sulfate | 1.4 |
| Sodium carboxymethyl cellulose | 1.0 |
| Sodium saccarin | 0.15 |
| Sodium benzoate | 0.05 |
| Toothpaste flavor | 1.0 |
| Compound of Example 2 | 0.01 |
| Total | 100.0 |

Users of the powder toothpaste as prepared above, reported experiencing a cool/refreshing feeling in the mouth. There was no bitterness. The clean, cooling/refreshing sensation was long lasting and is a positive signal of effectiveness.

Embodiment 2—Gel Toothpaste

The ingredients listed below were mixed in a suitable mixing apparatus to prepare a gel toothpaste.

| Ingredient | Weight Percent |
| --- | --- |
| sodium bicarbonate | 97.69 |
| magnesium oxide | 0.50 |
| flavor | 1.00 |
| Compound of Example 2 | 0.01 |
| polyethylene glycol | 0.50 |
| sodium saccharin | 0.20 |
| sodium triphosphate | 0.10 |
| Total | 100.0 |

Users of this gel toothpaste reported experiencing a cool/refreshing feeling in the mouth. There was no bitterness. The clean, cooling/refreshing sensation was long lasting and is a positive signal of effectiveness.

Embodiment 3—Chewing Gum

A chewing gum was prepared by first heating and melting the gum base in a high shear gum mixer. The corn syrup, glycerin and half the 10× sugar were added to the gum. The mixture was heated and stirred while the remainder of the sugar was added. Then, the flavor and the compound of the present invention were added until the mixture was uniform. As a final step, the uniform mixture was rolled out on a marble slab and cut into appropriate sizes.

| Ingredient | Weight Percent |
| --- | --- |
| gum base | 24.0 |
| corn syrup 42DE | 6.7 |
| Glycerin | 1.1 |
| 10X sugar | 67.19 |
| Chewing gum flavor | 1.0 |
| Compound of Example 2 | 0.01 |
| Total | 100.0 |

The chewing gum as prepared above had a cool/refreshing feeling with no bitterness. Compared to chewing gum which did not use a compound of the present invention, the chewing gum as prepared above had a longer lasting cool/refreshing flavor ith an impression of a prolonged flavor impact.

Embodiment 4—Hard Candy

A hard candy was prepared by combining all the ingredients listed below in a copper kettle. The color, flavor ("Cider flavor E-7004" Takasago International Corporation) and acid were mixed well, heated and melted at 230° F. The final mixture was poured into molds and allowed to cool.

| Ingredient | Weight Percent |
|---|---|
| Sugar | 51.9 |
| Water | 12.1 |
| Corn Syrup 42DE | 34.6 |
| Caramel Color | 0.89 |
| Flavor-Cider Flavor E-7004 | 0.1 |
| Citric Acid | 0.4 |
| Compound of Example 2 | 0.01 |
| Total | 100.0 |

Compared to hard candy which does not blend the compound of the present invention, there was a marked refreshing, longer lasting, non-bitter, coolness quality due to the inclusion of the compounds of the present invention.

Comparative Example

The enantiomeric compounds of the present invention, Examples 1 through 3 (E1, E2 and E3), were tested against the prior art racemic mixture of 2-(5-methyl-2-(methylethyl)-cyclohexyloxy)-ethan-1-ol (C1). Six evaluators swished 10 ml of a 150 ppm solution of each compound for 15 seconds and spit out. The quality of the flavor and cooling characteristics were reported at various intervals after spitting out. The results are summarized in the following table:

| Compound Name | | 1–5 Minutes | 10–15 Minutes | 30 Minutes |
|---|---|---|---|---|
| C1 | 2-(5-methyl-2-(methylethyl)-cyclohexyloxy)-ethan-1-ol | initially slightly cool, builds to medium intensity at 5 min., non-mentholic and bitter flavor | cooling intensity decreasing, lasting 10–15 min. | no cooling |
| E1 | (1R,2S,5R)-2-(5-methyl-2-(methyethyl)-cyclohexyloxy)-ethan-1-ol | initially slightly cool, clean, slight bitter and mentholic taste, cooling increased at 3–4 mins. | Peak cool at 15 min., clean, pleasant, non-medicinal | cooling |
| E2 | (1R,2S,5R)-3-(5-methyl-2-(methylethyl)-cyclohexyloxy)-propan-1-ol | immediately cool, very clean, very slight medicinal and bitter, good good at 1 min. | Peak cool at 10–13 mins., clean, fresh, non-mentholic | strong cooling 30+ min. |
| E3 | (1R,2S,5R)-3-(5-methyl-2-(methylethyl)-cyclohexyloxy)-butan-1-ol | slight immediate cool, initial bitter and medicinal taste, cooling increases from 3–5 mins. | Peak cool at 7 mins., "tingling" cool sensation | cooling |

The single enantiomer compounds of the present invention provide a cool/refreshing feeling. Compared with known compounds, they have a longer lasting cooling/refreshing effect. Since food, beverage, cosmetic and other products containing a compound of the present invention have longer lasting cooling and refreshing properties, the value of these products is increased.

Having described preferred embodiments of the present invention, it is to be understood that the invention is not limited to those precise embodiments, and that various changes and modifications may be effected therein by one skilled in the art without departing from the scope or spirit of the invention as defined in the appended claims.

What is claimed is:

1. A cooling sensate compound having the following general formula:

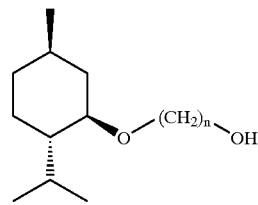

wherein n is an integer from 2 to 3.

2. A cooling sensate compound according to claim 1, wherein said compounds is the compound having the formula:

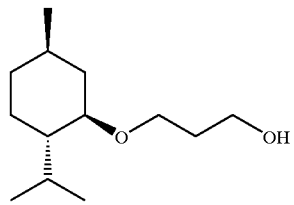

3. A cooling sensate compound according to claim 1, wherein said compound is (1R,2S,5R)-2-(5-methyl-2-(methyethyl)-cyclohexyloxy)-ethan-1-ol.

4. A cooling sensate composition comprising:
a compound of the following general formula:

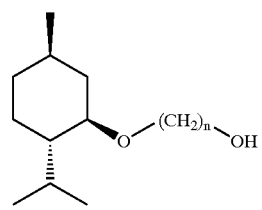

wherein n is an integer from 2 to 3; and
a suitable carrier.

5. A cooling sensate composition according to claim 4, wherein said compound is (1R,2S,5R)-2-(5-methyl-2-(methylethyl)-cyclohexyloxy)-ethan-1-ol.

6. A cooling sensate composition according to claim 4, wherein said compound is (1R,2S,5R)-3-(5-methyl-2-(methylethyl)-cyclohexyloxy)-propan-1-ol.

7. A cooling sensate composition according to claim 4, wherein said cooling sensate composition is a composition selected from the group consisting of a food additive, a beverage additive, a flavor additive, and a toiletry additive.

8. A cooling sensate composition according to claim 4, wherein said cooling sensate composition is a composition selected from the group consisting of a fruit juice, a fruit wine, a dairy drink, a carbonated drink, an ice cream, a sherbet, an ice candy, a jelly, a hard candy, a chewing gum, a mouth wash, a toothpaste, a tooth gel, a cough drop, a nebulizer, a perfume, an eau de toilette, a cologne, an after shave, a deodorant, an antiperspirant, a hand cream, a shampoo, and a soap.

9. A cooling sensate composition according to claim 4, further comprising at least one additional sensate material.

10. A method of using a compound according to formula (I)

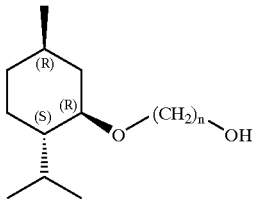

(I)

wherein n is an integer from 2 to 3, as a cooling sensate, comprising:

adding an effective amount of a compound of formula (I) to a member selected from the group consisting of a food additive, a beverage additive, a flavor additive, a toiletry additive, and any combination of any of the foregoing.

11. A method of using a compound of formula (I) of claim 10, wherein said food additive, said beverage additive, said flavor additive, and said toiletry additive is selected from the group consisting of a fruit juice, a fruit wine, a dairy drink, a carbonated drink, an ice cream, a sherbet, an ice candy, a jelly, a hard candy, a chewing gum, a mouth wash, a toothpaste, a tooth gel, a cough drop, a nebulizer, a perfume, an eau de toilette, a cologne, an after shave, a deodorant, an antiperspirant, a hand cream, a shampoo and a soap.

12. A method of using a compound of formula (I) of claim 10, wherein said compound is (1R,2S,5R)-2-(5-methyl-2-(methylethyl)-cyclohexyloxy)-ethan-1-ol.

13. A method of using a compound of formula (I) of claim 10, wherein said compound is (1R,2S,5R)-3-(5-methyl-2-(methylethyl)-cyclohexyloxy)-propan-1-ol.

* * * * *